United States Patent [19]
Chen

[11] Patent Number: 5,852,489
[45] Date of Patent: Dec. 22, 1998

[54] DIGITAL VIRTUAL CHIASM FOR CONTROLLED STIMULATION OF VISUAL CORTICES

[76] Inventor: Chi Chen, 16 Brittany Cir., Rochester, N.Y. 14618

[21] Appl. No.: 997,133

[22] Filed: Dec. 23, 1997

[51] Int. Cl.[6] ........................................... A61B 3/00
[52] U.S. Cl. ............................................... 351/237
[58] Field of Search ........................... 351/200, 204, 351/205, 206, 208, 209, 210, 237; 382/103, 291; 348/78

[56] References Cited

U.S. PATENT DOCUMENTS

| | | | |
|---|---|---|---|
| 5,491,757 | 2/1996 | Lehmer et al. | 351/210 |
| 5,583,795 | 12/1996 | Smyth | 702/150 |
| 5,644,642 | 7/1997 | Kirschbaum | 382/103 |

*Primary Examiner*—George Manuel
*Attorney, Agent, or Firm*—Howard J. Greenwald

[57] ABSTRACT

A digital virtual chiasm apparatus for controlled stimulation of visual cortices, which contains an eye tracker, a digital computer, and a display device. The apparatus is capable of generating a first set of stimuli in a first half visual field while simultaneously generating a second set of stimuli in second, contralateral half visual field and a boundary between said first half visual field and said second half visual field. It is also capable of moving the boundary between the first half visual field and the second half visual field in response to eye movement of the subject.

18 Claims, 5 Drawing Sheets

DIGITAL VIRTUAL CHIASM FOR CONTROLLED STIMULATION OF VISUAL CORTICES

FIELD OF THE INVENTION

An apparatus and process for delivering timed visual stimuli to specified cortical areas in each hemisphere of the brain of either a human or a higher primate subject.

BACKGROUND OF THE INVENTION

The human visual system, and indeed that of all higher primates, has a unique organization in that retinal cells to the left of the fovea in each eye "viewing" the right half visual field project to the left visual cortex, and those to the right of the fovea project to the right cortex. This peculiar division is achieved via the crossing of the nerve fibers in the nasal half of each eye just as they enter the skull, in a structure at the base of the brain called the optic chiasm, while the fibers from the lateral or temporal half of each eye do not cross but pass directly to the brain on the same side that they enter. The visual scene shifts constantly as the eyes move in natural viewing. Objects in a visual scene are examined by different populations of retinal cells and thus different groups of cortical neurons distributed in the two halves of the brain. It is known, however, that despite the rich interconnections between the two, each half of the brain is significantly different from the other, and each seems to specialize in certain functions which the other performs with varying degrees of difficulty. The hemispheric specialization or laterality is supported by experimental evidence from "split-brain" patients or pathology within a particular hemisphere. The left hemisphere is frequently referred to as language-dominant, the right as spatial-orientation- or emotion-dominant.

Under this situation it would be highly desirable to deliver visual stimuli exclusively to one or the other cerebral hemisphere to test the unique functions of each. Up to the present time this has been possible with 200-millisecond tachistoscopic views flashed in one or the other half visual field while the subjects hold their eyes steady upon a central point. U.S. Pat. Nos. 3,498,700, 3,526,455, and 5,147,205 relate to tachistostopic devices; the entire disclosure of each of these patents is hereby incorporated by reference into this specification. A common and serious problem with using such devices is that longer exposure of the stimuli is not feasible, since, if the subjects move their eyes, as they can if allowed more than 200 milliseconds to do so, the stimuli will not be confined to the selected half visual field. Thus, a task can not be administered on a level of reasonable complexity compatible with even normal functioning of the visual system. Any eye movement may invalidate a trial. It is difficult and impossible sometimes for certain subjects to maintain a central fixation as required. In spite of many problems with the tachistoscopic technique, it has been used for many decades by numerous investigators in many fields such as psychology, neurophysiology, and psychiatry, etc. simply because there have been no better alternatives. Interpretation of results is frustrating and heavily dependent upon statistics due to the technological shortcomings.

Attempts have been made to provide a substantially improved device, to no avail. Thus, U.S. Pat. No. 4,726,673 describes electro-optical valves attached to special spectacles worn by the subject. U.S. Pat. No. 5,137,018 discloses a method of using filters attached on spectacles to deliver visual stimuli at different wavelengths to the two hemispheres. U.S. Pat. No. 5,424,786 makes use of spectacles with half-opaque, half-transparent lenses to block half of the view. The apparatus disclosed in U.S. Pat. No. 5,562,719 is a box containing four compartments with a light source in each; the subject looks into the box, and light sources corresponding to a selected half visual field are turned on to achieve a therapeutic purpose. The disclosure of each of these United States patents is hereby incorporated by reference into this specification.

However, all of the methods and devices described in these prior art patents suffer from at least one major disadvantage—they fail if the eyes move. It is simply impossible to achieve an acceptable separation of the two half visual fields through any blocking technique using these devices.

The problems with the prior art devices are summarized in U.S. Pat. No. 5,589,897, the entire disclosure of which is hereby incorporated by reference into this specification. However, all this patent summarizes the problems, it does not provide any solutions to them which are effective in overcoming the major disadvantage discussed above.

U.S. Pat. Nos. 4,059,349 and 5,220,361, the entire disclosures of which is hereby incorporated by reference into this specification, disclose machines in which eye movements are taken into account in the presentation of a simple light-spot onto the retina. The devices disclosed these patents are incapable of presenting words and pictorial materials to the visual field as required.

In an article by Norman C. Nettleton et al. entitled "A Moving Video Window or Mask Yoked to Eye Movements: A System to Permit Free Ocular Scanning within Delimited Areas of the Visual Field," which was published in Behavior Research Methods & Instrumentation, Vol. 15, No. 5, pp. 487–496, 1983. A review of lateralized stimulation techniques was presented. The authors of this paper proposed a system incorporating a commercial eye tracker and home-made analog circuits including a Saw-tooth Generator and Analog to TTL Interface Circuit, a Video Gating Logic and Line Generator, and a Video/sync Combining Circuit. The gaze-tracking display is based on and controlled by analog hardware techniques. Half of the display area is simply blanked. No field switching is possible during an experiment. It is cumbersome to setup, adjust, and calibrate such a system. No further report has been found in the implementation and use of the system.

In a paper by Paul M. J. van Diepen, titled "On-line Control of Moving Masks and Windows on a Complex Background using the ATVista Videographics adapter," which was published in Behavior Research Methods, Instruments, & Computers, Vol. 26, No. 4, pp. 454–460, 1994, a device for gaze following display was discussed. However, the device of this article does not enable one to present stimuli to a hemisphere selectively. A special videographics adapter is necessary for the system to function. The background display must come from either a camera directly or a second computer with the second special videographics adapter installed in it. Most controls require definitely an obsolete operating system to operate.

To enable free eye movements in hemispheric viewing, limited surgical procedures have been applied to animals. In the monkey having undergone chiasmotomy, for example, the crossing nerve fibers are sectioned at the optic chiasm and stimuli from each eye to the contralateral hemisphere are eliminated. It can be easily imagined that the monkey sees half of the visual scene only in monocular viewing. The other half is blanked as if a half-shutter follows the gaze at all times. It is noted that chiasmotomy, which easily achieves the limitation of visual input to one or the other hemisphere simply by covering one or the other eye, introduces a serious abnormality in that approximately 50% of the optic nerve fibers are destroyed, i.e., chiasmotomy produces blindness in the lateral half of the visual field.

The major problems with the prior art become obvious heretofore. The traditional tachistoscopic technique delivers unrealistically short and simple stimuli without any eye movement allowed. All prior gaze following apparatus and methods depend on special purpose hardware in addition to an eye tracker to block one half visual field selected before a test with very poor precision, reliability, and flexibility. The surgical procedure is reliable but invasive and irreversible.

It is an object of this invention to provide an apparatus which overcomes the aforementioned shortcomings of the prior art device. The device of this invention takes advantage of the most recent digital image processing technology, the multi-process and multi-thread feature of the latest Microsoft Windows 95 or Windows NT 4.0 operating system, and the fast and popular Pentium II 300 MHz based PC workstation. The disclosed machine is the first software-based solution which makes it possible to execute the disclosed process the first time with a pixel level spatial precision and a millisecond level time resolution. The display itself is updated through executing software routines following the eye position to achieve the hemispheric and localized stimulation. The physician or the experimenter conducting a test may examine freely on the same display screen what is currently fed to the two cerebral hemispheres of the subject. Neither special purpose hardware nor modified spectacles are needed.

SUMMARY OF THE INVENTION

In accordance with this invention, there is provided a digital virtual chiasm apparatus for the controlled stimulation of visual cortices. Said apparatus comprises a means tracking eye movement, a digital computer, a computer monitor, a first input panel, a second input panel.

The device of this invention, and the process which utilizes it, allow subjects (human or higher primates) to perceive a scene using natural eye movements and the full half-field of view, while restricting direct visual input to a chosen hemisphere at any time for a period that the experimenter can freely specify. The complexity of the stimulus is no longer a limiting factor as with the tachistoscopic technique. Therefore, an investigation may take advantage of an adjustable level of the complexity that the claimed device delivers. In realizing the fact that all visual inputs converge to the optic chiasm before reaching the cortices, and that the surgical intervention site is at the chiasm, the claimed device functions as a virtual visual input traffic controller at the chiasm. The process selectively directs visual stimuli to a specified hemisphere or region of the brain at the experimenter's will with the biological chiasm and the subject intact. This invention employs the most recent digital technology to update displays in both half visual fields directly in real time based on the current eye position.

This device of this invention applies in basic research on the manner of brain organization in fully intact human or monkey subjects, and in diagnostic use for determining functional capabilities or normality of the two halves of the brain in conditions such as stroke, traumatic brain injury, developmental dyslexia or schizophrenia. It also has utility for rehabilitation where there is an abnormality in the working between the two cerebral hemispheres, or in orthoptic training in cases of strabismus. The bases behind the diagnostic and therapeutic theaters are: 1) A deficit revealed by a localized stimulus probe manifests possible lesion sites more accurately; and 2) Receiving inputs directly in an affected area may stimulate its recovery when chances exist, or seeking a more effective compensation from the contralateral counterpart by evading a dominant but impaired hemisphere. This invention obviates the necessity of surgical isolation of the visual pathways in monkeys, thereby allowing experiments on a filly normal rather than neurologically impaired animal; and it can not only serve as a tachistoscope for experiments using human subjects, but offers a major improvement, in that linkage to eye position assures the laterality of the presented stimuli.

BRIEF DESCRIPTION OF THE DRAWINGS

The invention will be described by reference to the specification and the following drawings in which like numbers refer to like elements, and in which.

DESCRIPTION OF THE PREFERRED EMBODIMENT

Figure 1:
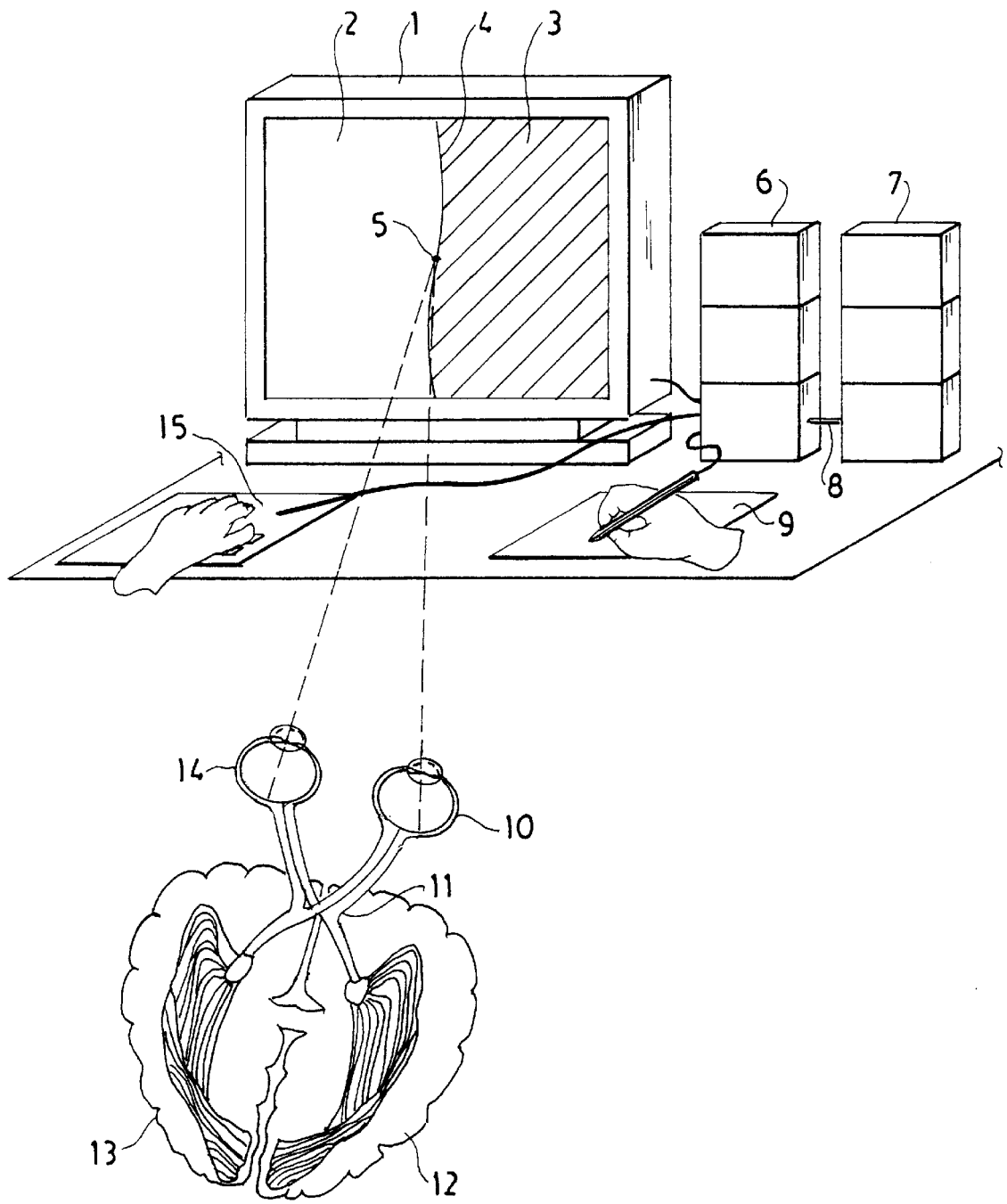
FIG. 1 is a schematic view of a preferred apparatus of the invention.

FIG. 1 is a schematic representation of one preferred digital virtual chiasm (DVC) apparatus 20. In the remainder of this specification, the abbreviation DVC will be used to refer to this claimed apparatus 52.

Referring to FIG. 1, it will be seen that DVC 52 is comprised of an eye tracker 7. As is apparent to those skilled in the art, a eye tracker is device for measuring the movement of an eye.

One may use any of the eye trackers described in the prior art. Thus, by way of illustration and not limitation, one may use one or more of the eye trackers described in U.S. Pat. No. 5,471,542 (point of gaze eye tracker), U.S. Pat. No. 4,702,575 (helmet-mounted eye tracker), U.S. Pat. No. 4,648,052 (eye tracker communication system), U.S. Pat. No. 4,373,787 (three dimensional eye tracker), U.S. Pat. No. 4,287,410 (double purkinje eye tracker), U.S. Pat. No. 3,804,496 (two dimensional eye tracker), U.S. Pat. Nos. 3,724,932, 3,712,716, and the like. The disclosure of each of these United States patents is hereby incorporated by reference into this specification.

By way of further illustration, a review on eye trackers is presented in an article by L. R. Young and D. Sheena, entitled "Survey of eye movement recording methods," which appeared in Behavior Research Methods & Instrumentation, Vol. 7, pp. 397–429, 1975).

In one preferred embodiment, a eye tracker manufactured by the ISCAN Company of Boston, Mass. is used. This eye tracker is described, e.g., in U.S. Pat. No. 5,103,306, the entire disclosure of which is hereby incorporated by reference into this specification.

In another embodiment, a Robinson Search Coil eye tracker is used. Search coil eye trackers are well known to those skilled in the art and are described, e.g., in U.S. Pat. No. 5,558,091 (see, e.g., the Ronald S. Remmel article referred to therein), U.S. Pat. Nos. 5,382,989, 4,993,825, 4,988,183, 4,494,553, and the like. The disclosure of each of these United States patents is hereby incorporated by reference into this specification.

Referring again to FIG. 1, and in the preferred embodiment depicted therein, it will be seen that a digital computer 6 is used in the system. The computer 6 preferably contains a "PENTIUM II" microprocessor with a speed of at least about 300 megaHertz and containing at least 32 million bytes of random access memory; it preferably is a Pentium II based workstation.

"PENTIUM" processors are well known to those skilled in the art and are described, e.g., in U.S. Pat. Nos. 5,613,087, 5,404,559, 5,653,863, and the like. The disclosure of each of these United States patents is hereby incorporated by reference into this specification.

Referring again to FIG. 1, it be seen the DVC system also is comprised of computer monitor 1. It is preferred that the monitor 1 have a refresh rate of at least 200 hertz. The term "refresh rate" is well known to those skilled in the art and is disclosed, e.g., in U.S. Pat. No. 4,511,892, the entire disclosure of which is hereby incorporated by reference into this specification.

Referring again to FIG. 1, it will be seen that the DVC system 52 also comprises a manually operated input device 15, such as a button response panel and/or a computer mouse. Furthermore, DVC system 52 also comprises another input device, such as light pen 9. Depending upon the stimulus presented to the subject, and the response(s) desired, the subject will use either one or both of such input devices. The two input panels can be positioned anywhere as required.

Referring again to FIG. 1, it will be seen that the graphics display on the monitor screen 1 is preferably divided into a left half visual field 2 and a right half visual field 3. As will be apparent to those skilled in the art, although the area of visual field 2 may be equal to that of field 3, it will not necessarily be.

The two half visual fields 2 and 3 are updated by following the gaze 5 in real time. The gaze is a fixation point 5 for the subject 50. The dividing line 4 or curve 4 between visual fields 2 and 3 is determined using readily available data on the retinal division.

The functions of the DVC 52, and the process utilizing it, are realized by executing a software program package under the Microsoft Windows 95 or Windows NT 4.0 operating system on the host workstation 6.

One preferred computer program which can advantageously be used with the DVC system is enclosed as at the end of applicant's specification. It will be apparent that multiple threads of this program run simultaneously.

The root thread is primarily responsible for presenting and updating the displays in the two half visual fields 2 and 3. An eye position monitor thread is created by the root thread during the program initialization period and runs independently after its creation. It constantly monitors a serial port (not shown) of the host workstation 6. Eye position data are sent to this port by the eye tracker (7) through a serial cable 8. The eye position monitor thread responds to any new available data item corresponding to the current eye position and forwards calibrated data to the root thread through a channel of inter-thread communication. The root thread updates a minimal area that must be re-drawn on the monitor screen 1 based on the current and the last eye positions detected. A minimal amount of time is spent on updating both half visual fields 2 and 3. A performance monitor thread is also created in the initialization phase by the root thread. It monitors the time spent by the root thread in updating the display. If the time exceeds 1 millisecond under extremely rare conditions, the operator is warned and the trial record is marked. The visual field updating operation is data-driven by design. The data availability rate at the eye tracker 7 determines the display-updating rate. If a 200 Herz ISCAN eye tracker is used, for example, the display is updated every 5 milliseconds. The root thread spends up to 1 millisecond to complete the updating related computation each time.

Figure 2A:
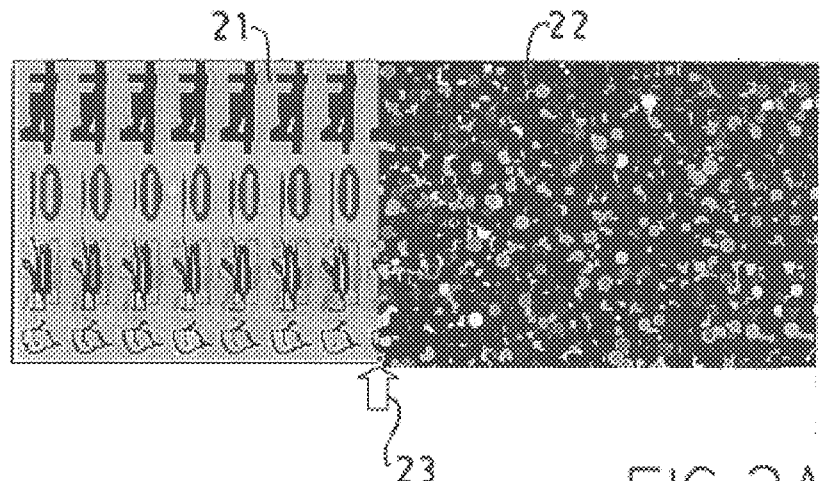
FIGS. 2A, 2B, and 2C illustrate one typical changing display provided by the apparatus of FIG. 1 as a subject eyes move.

To update the two half visual fields 2 and 3 in a minimal amount of time, a minimal display area needs to be identified first and re-painted subsequently. Referring to FIG. 2A, the right hemisphere 12 (see FIG. 1) is stimulated by a primary stimulus 21 and the left hemisphere 13 (see FIG. 1) by a secondary stimulus 22 when the gaze (not shown in FIG. 2, but see FIG. 1) falls exactly on the dividing line 23. If the next data item from the eye tracker indicates the gaze has moved leftward to line 24 in FIG. 2B, the minimal area to be updated using the secondary stimulus is delimited by line 23 and line 24. The root thread re-paints this area only in order to save time. Subsequently, if the gaze moves rightward to line 25 in FIG. 2C, the root thread re-paints another minimal area delimited by line 24 and line 25 using the primary stimulus. As the process continues, the contents of stimuli are changed according to the experimental protocol used. The primary and the secondary stimuli 21 and 22 are swapped as frequently as required during a test. Although FIGS. 2A, 2B, and 2C exemplify how the two half visual fields are updated in this invention, they are illustrate a visual memory test paradigm, i.e., an implementation of a modified hemianopia using the DVC 52. A traditional hemianopia is realized by simply blacken the secondary stimulus 22; the superiority in using a secondary stimulus 22 is to be able to condition the "non-viewing" hemisphere. The conditioning pattern is selected to produce maximal irrelevant activity in the "non-viewing" hemisphere to reduce its processing of signals from the "viewing" hemisphere. In a test, a series of similar stimulating pictures is presented following an accurate time sequence previously defined. Each of the two cerebral hemispheres is stimulated or conditioned randomly.

Figure 2B:
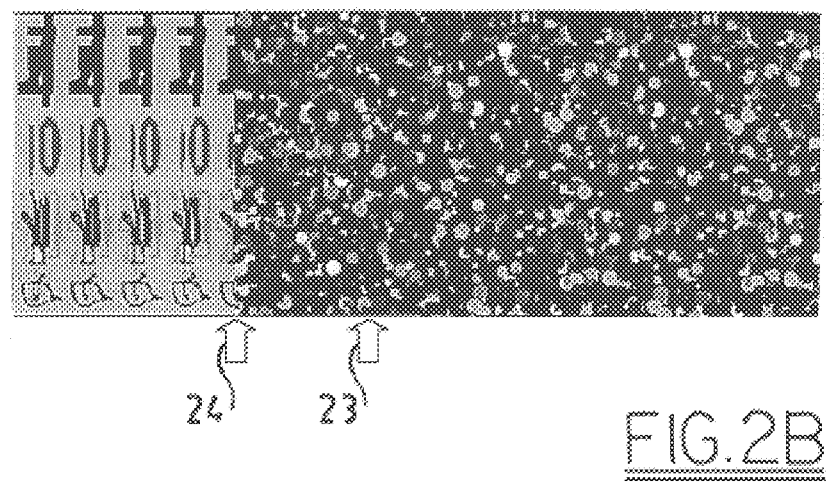
Figure 2C:
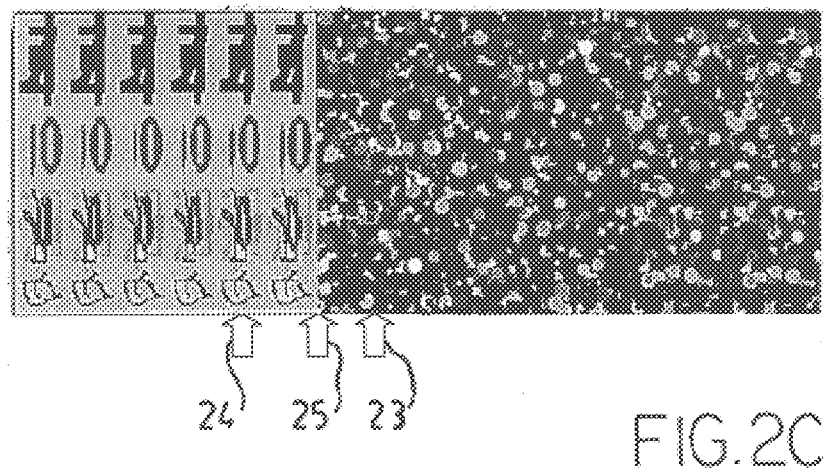

Regarding the dividing line 23 between the left and right half visual fields 21 and 22 in FIGS. 2A, 2B, and 2C, the clear-cut, vertical division is not normally apparent to the subject. Furthermore, a slight overlap between the two fields remains a possibility. The functional extent of this overlap is difficult to define although it seems functionally negligible. There is also an inter-subject variation regarding the curvature of the line. In cases where a curved division is preferable, the DVC scales and positions such a curve in between the two visual fields on display based on information specific to a subject, the distance from the eye to the display, as well as the eye position. The root thread updates a polygonal area rather than a rectangle area each time. The DVC is made capable of positioning the dividing line or curve a distance away from the gaze at a resolution step of one pixel. In all drawings used in this document such a dividing line can be taken as a curve in general whenever necessary.

Figure 3A:
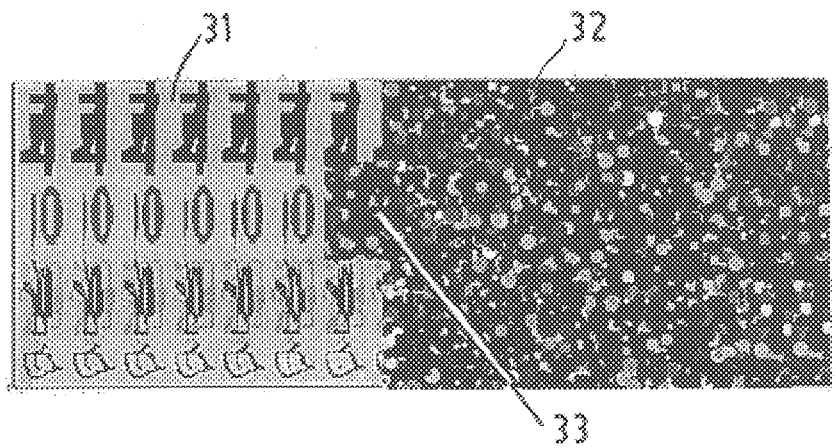
FIGS. 3A and 3B illustrate another typical changing display provided by the the apparatus of FIG. 1 as a subject eyes move.
Figure 3B:
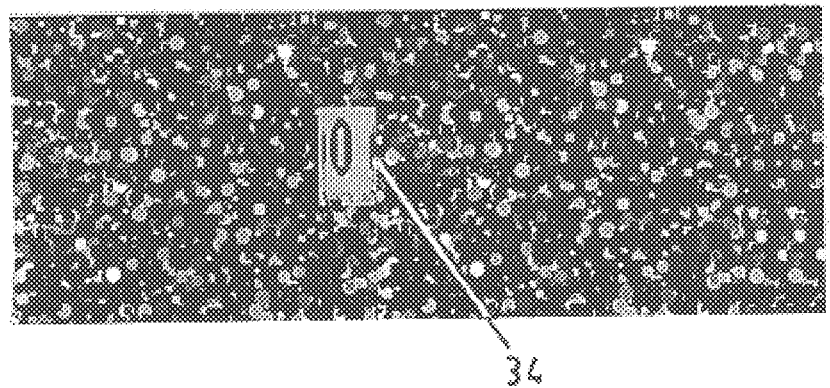

Another two related new paradigms are disclosed in FIGS. 3A and 3B. FIG. 3A depicts a test in which an entire hemisphere and foveal vision of the contralateral hemisphere are conditioned or masked. The primary stimulus 31 is delivered to the peripheral vision area of the right hemisphere. The DVC follows the gaze 33 to where it lands and updates affected areas in both half visual fields in real time as disclosed early in this document. The foveal visual area of the right hemisphere and the entire left hemisphere is conditioned by a secondary stimulus 32. By the same token peripheral vision is similarly masked in FIG. 3B. The primary stimulus is directed to the foveal visual area of the right hemisphere exclusively. When the gaze 34 moves, different parts of the primary stimulus are sent to the right brain through the traffic tunnel created using the DVC. An imaginary equivalence is that nerve fibers at the chiasm are selectively switched on and off for conducting. The DVC simply turns an impossible surgery into a reality. In addition, a similarly limited stimulating window can be positioned anywhere on the retina. The DVC imitates, in one or both eyes, clinical conditions, such as macular degeneration or retinitis pigmentosa, where either sharp foveal vision or "wide field" vision, respectively, is lost or degraded.

Eye movements normally accompany the examination of a visual scene. Objects in the scene are scanned by more neurons due to these movements. When he DVC is required to create a "sticky scene" that follows the eyes, the root thread simply re-draws the scene corresponding to the eye movements. The penalty in recognition and memory will be revealed by this paradigm.

Figure 4A:
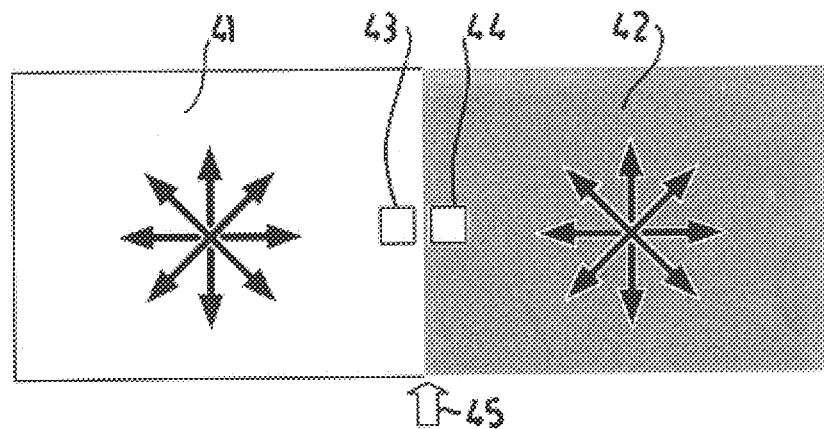
FIGS. 4A and 4B illustrate yet other typical displays provided by the apparatus of this invention.

It is interesting to contemplate an evolutionary outcome that dim-light-sensitive rod cells are distributed outside the foveal area of the retina. While the "mind" is attentive to a main visual object, e.g., an escaping prey target, pursued by foveal vision, impulses from these rods may still be interpreted as either an approaching danger, e.g., a predator or a projectile threat, from certain direction or something else that can be ignored for the moment. The DVC simulates the case in a controllable manner as shown in FIG. 4A. As an attention-demanding task proceeds in a small window 43 (or 44) in a half visual field, object motion in a specified direction is presented briefly at one of a few controlled eccentricities in the same field 41 (or 42) or the contralateral half field 42 (or 41). A response monitor thread collects subject responses from the button response panel 15 and the light pen input panel 9 shown in FIG. 1. Is there any difference between the two hemispheres in initiating an attention shift if any? Is the right hemisphere apparently associated with spatial-orientation dominance superior in recognizing the direction of motion? Obviously, the availability of the DVC to the whole neurological community may create a unique opportunity for a new generation of experimental paradigms and protocols, which may subsequently lead to definitive answers to many questions.

Figure 4B:
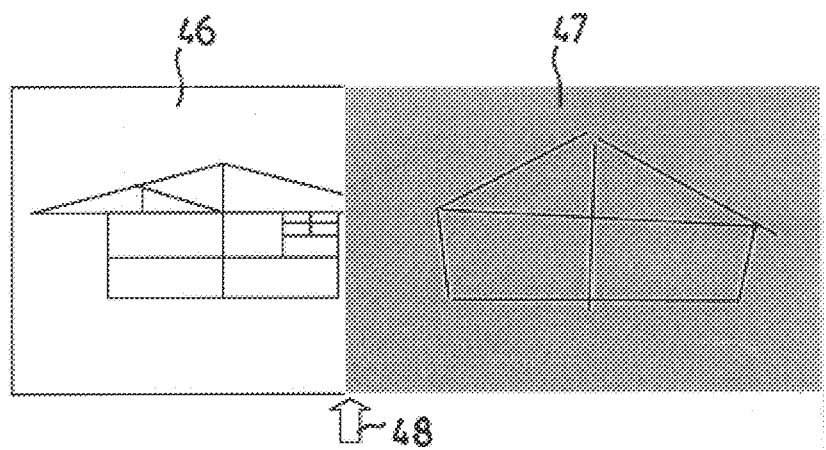

In investigations of laterality and bihemispheric communication, the DVC 52 directs different primary and secondary stimuli to the two halves of the brain in any order or combination. A proper use of the primary and secondary pair in sequence may prove to be beneficial because its "push-pull" effect may actually magnify hemispheric propensity for the purpose of an increased detectability. The DVC also monitors responses from each of the two hemispheres in order to facilitate interactive and self-administered procedures, which might be crucial in capturing minute differences between the two halves in a series of hemispheric switching tasks. The digital nature of the DVC makes it possible to implement these procedures. Regarding FIG. 4B the DVC presents a line drawing in the left half visual field 46 exclusively. This drawing is thus delivered to the subject's right hemisphere. The subject task is to copy the drawing into the right half visual field. The response monitor thread records the light pen or a mouse position and passes data to the root thread, which displays the subject drawing in the right half visual field. Both half fields are updated exactly the way as disclosed early in this document. For instance, the right half field must cover part of the original drawing when the gaze falls along line 48. Otherwise, this part will "leak" into the contralateral hemisphere erroneously. It is noted that a typical neuropsychological assessment test is conducted in an unprecedented, hemispheric way using the DVC 52.

Referring again to FIG. 1, it will be seen that an eye-tracker 7 is a necessary component of the DVC system 52. The DVC 52 is designed to accept any commercially available eye tracker.

Although many digitial computers may be used for the host workstation 6 of the DVC 52, it is preferred to use a popular platform, e.g., Microsoft Windows 95 or Windows NT 4.0, on a Pentium II PC workstation. The use of such hardware outweighs the performance to be gained by using a less popular, more expensive hard real-time operating system such as LynxOS or QNX on Unix work stations. The DVC 52 is actually preferably built using most popular computing components. Literally, any one can set it up and run it in a few minutes. Its "user-friendly" nature is further enhanced by an auto-calibration routine as part of the software package. During the calibration phase, the routine presents a disk with a centered cross hair at a series of locations on the screen. The subject is asked to fixate on the cross hair briefly and press a button. The routine calculates a few coefficients and saves them in a file. The eye position monitor thread corrects eye position data using these coefficients each time a new data item comes in from the eye tracker.

A Preferred Computer Program for use with Applicant's Claimed Apparatus

Figure 5:
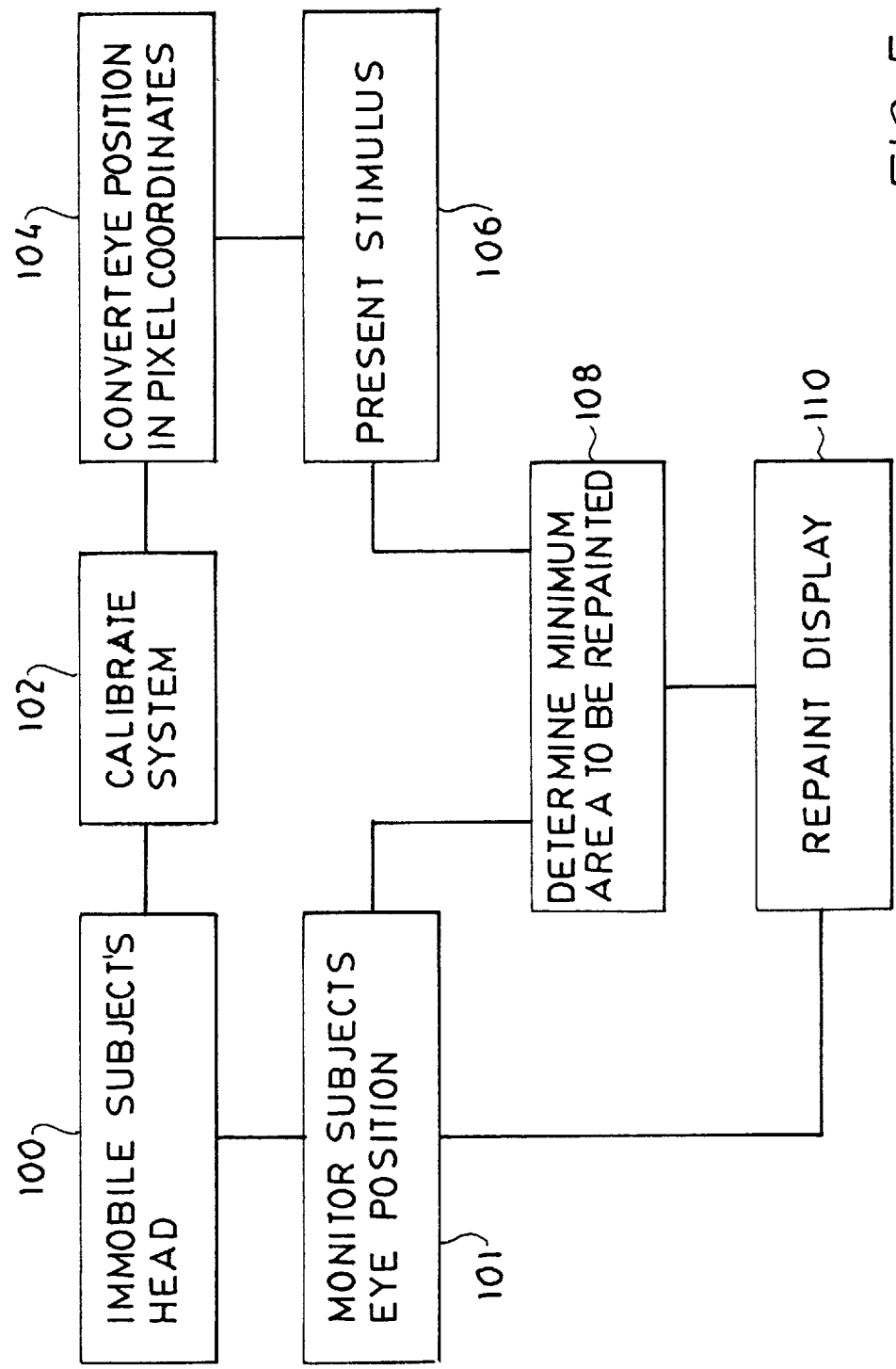
FIG. 5 is a flow diagram illustrating a preferred process of the invention.

By way of illustration and not limitation, one may use the following computer program together with applicant's claimed device A Preferred Process of the Invention FIG. 5 is a flow diagram of one preferred process of the invention. Referring to FIG. 5, and in step 100 thereof, the subject's head is immobilized by conventional means so that, during his evaulation, he cannot readily move his head. Thereafter, in step 102, the DVC system 52 is calibrated by using an autocalibration program such as, e.g., the program described in this specification; factors such as the distance of the subject from the monitor, the distance between the subject's pupils, the relative elevation of the subject vis-a-vis the monitor, and the like are taken into account during this calibration step.

One the subject's head has been immobilized, and thereafter, the subject's eye position is monitored in step 101 by means of the eye tracker.

Thereafter, in step 104, the subject's eye position is translated into pixel coordinate pairs which reflect actual location of the display. Subsequently, in step 106, stimuli presentation is commenced according to the subject's current eye position by presenting the first stimulus.

Based upon the subject's current eye position (as determined in step 101), in step 108 the system determines the minimal area to be repainted in the display based upon the subject's current and last eye position. Thereafter, in step 110, the display is repainted. The sequence is then again repeated with the monitoring of the subject's eye position in step 101, the presentation of the stimulus in step 106, the determination of the minimal area to be repainted in step 108, and repainting of the display in step 110.

In the preferred embodiment, because of the speed of the computer 6 and the fact that generally there will only be a minimal area to be repainted, the subject should be unaware e of any change in the display presented to him.

It is to be understood that the aforementioned description is illustrative only and that changes can be made in the apparatus, the ingredients and their proportions and in the sequence of combinations and process steps, as well as in other aspects of the invention discussed herein, without departing from the scope of the invention as defined in the claims.

I claim:

1. A digital virtual chiasm apparatus for controlled stimulation of visual cortices, wherein said apparatus comprises a means for tracking the eye movement of a subject, a digital computer operatively connected to said means for tracking the eye movement of a subject, a display operatively connected to said digital computer, means for generating a first set of stimuli in a first half visual field while simultaneously generating a second set of stimuli in second, contralateral half visual field and a boundary between said first half visual field and said second half visual field, and means for moving said boundary between said first half visual field and said second half visual field in response to the eye movement of said subject.

2. The apparatus as recited in claim 1, wherein said digitial computer is comprised of a microprocessor with a speed of at least about 300 megaHertz.

3. The apparatus as recited in claim 1, wherein said display is a computer monitor.

4. The apparatus as recited in claim 3, wherein said computer monitor has a refresh rate of at least about 200 Hertz.

5. The apparatus as recited in claim 4, wherein said apparatus further comprises a first manually operated input device.

6. The apparatus as recited in claim 5, wherein said first manually operated input device is a button response panel.

7. The apparatus as recited in claim 6, wherein said apparatus is comprised of a second manually operated input device.

8. The apparatus as recited in claim 7, wherein said second manually operated input device is a light pen.

9. The apparatus as recited in claim 7, wherein said second manually operated input device is a computer mouse.

10. A process for providing controlled stimulation of visual cortices, comprising the steps of:

(a) providing an apparatus comprising us comprises a means for tracking the eye movement of a subject, a digital computer operatively connected to said means for tracking the eye movement of a subject, and a display operatively connected to said digital computer, (b) generating a first set of stimuli in a first half visual field while simultaneously generating a second set of stimuli in second, contralateral half visual field and a boundary between said first half visual field and said second half visual field, and (c) moving said boundary between said first half visual field and said second half visual field in response to the eye movement of said subject.

11. The process as recited in claim 10, wherein said digitial computer is comprised of a microprocessor with a speed of at least about 300 megaHertz.

12. The apparatus as recited in claim 10, wherein said display is a computer monitor.

13. The apparatus as recited in claim 12, wherein said computer monitor has a refresh rate of at least about 200 Hertz.

14. The apparatus as recited in claim 13, wherein said apparatus further comprises a first manually operated input device.

15. The apparatus as recited in claim 14, wherein said first manually operated input device is a button response panel.

16. The apparatus as recited in claim 15, wherein said apparatus is comprised of a second manually operated input device.

17. The apparatus as recited in claim 16, wherein said second manually operated input device is a light pen.

18. The apparatus as recited in claim 16, wherein said second manually operated input device is a computer mouse.

* * * * *